(12) United States Patent
Lim et al.

(10) Patent No.: US 11,246,532 B2
(45) Date of Patent: Feb. 15, 2022

(54) ELECTRONIC DEVICE

(71) Applicant: SAMSUNG DISPLAY CO., LTD., Yongin-si (KR)

(72) Inventors: Jae Ik Lim, Yongin-si (KR); Won Sang Park, Yongin-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 303 days.

(21) Appl. No.: 16/152,840

(22) Filed: Oct. 5, 2018

(65) Prior Publication Data

US 2019/0239808 A1    Aug. 8, 2019

(30) Foreign Application Priority Data

Feb. 5, 2018    (KR) .......................... 10-2018-0014204

(51) Int. Cl.
*A61B 5/00*      (2006.01)
*H01L 27/32*      (2006.01)
(Continued)

(52) U.S. Cl.
CPC .......... *A61B 5/6826* (2013.01); *A61B 5/0075* (2013.01); *A61B 5/0205* (2013.01);
(Continued)

(58) Field of Classification Search
CPC ... A61B 5/6826; A61B 5/0075; A61B 5/0205; A61B 5/1114; A61B 5/1124; A61B 5/1125; A61B 5/1126; A61B 5/1127; A61B 5/1128; A61B 5/742; A61B 5/02433; A61B 5/02438; A61B 2562/0238; A61B 5/024; A61B 5/02416; A61B 5/021;
(Continued)

(56) References Cited

U.S. PATENT DOCUMENTS

| 6,018,673 A * | 1/2000 | Chin ................... A61B 5/14552 356/41 |
| 6,388,247 B2 * | 5/2002 | Asada ..................... G01L 1/248 250/221 |

(Continued)

FOREIGN PATENT DOCUMENTS

| KR | 1020150032028 A | 3/2015 |
| KR | 1020170008498 A | 1/2017 |

OTHER PUBLICATIONS

S. Urban, J. Bayer, C. Osendorfer, G. Westling, B. B. Edin and P. van der Smagt, "Computing grip force and torque from finger nail images using Gaussian processes," 2013 IEEE/RSJ International Conference on Intelligent Robots and Systems, 2013, pp. 4034-4039, doi: 10.1109/IROS.2013.6696933 (Year: 2013).*

(Continued)

*Primary Examiner* — Shirley X Jian
(74) *Attorney, Agent, or Firm* — Cantor Colburn LLP

(57) ABSTRACT

An electronic device to be mounted around a finger includes: a top part on which a nail of the finger is located; a bottom part disposed opposite to the top part, where a fingerprint surface of the finger is located on the bottom part; and a side part connecting the top part and the bottom part to each other, where the top part generates a nail image by image-picking up the nail, and senses a movement of the finger, based on the nail image.

13 Claims, 8 Drawing Sheets

[Flexion]

[Extension]

(51) Int. Cl.
*A61B 5/11* (2006.01)
*A61B 5/0205* (2006.01)
*G06K 9/00* (2006.01)
*A61B 5/024* (2006.01)
*H01L 27/146* (2006.01)

(52) U.S. Cl.
CPC ........... *A61B 5/1114* (2013.01); *A61B 5/1128* (2013.01); *A61B 5/742* (2013.01); *G06K 9/0004* (2013.01); *H01L 27/3234* (2013.01); *A61B 5/02433* (2013.01); *A61B 5/02438* (2013.01); *A61B 2562/0238* (2013.01); *G06K 2009/0006* (2013.01); *G06K 2009/00939* (2013.01); *H01L 27/14678* (2013.01)

(58) Field of Classification Search
CPC ......... G06K 9/0004; G06K 2009/0006; G06K 2009/00939; H01L 27/3234; H01L 27/14678
See application file for complete search history.

(56) References Cited

U.S. PATENT DOCUMENTS

| | | | | |
|---|---|---|---|---|
| 6,845,256 | B2* | 1/2005 | Chin | A61B 5/14552 600/323 |
| 7,260,425 | B2* | 8/2007 | Chin | A61B 5/14552 600/323 |
| 7,720,516 | B2* | 5/2010 | Chin | A61B 5/6833 600/322 |
| 8,649,839 | B2* | 2/2014 | Chin | A61B 5/6833 600/324 |
| 9,891,718 | B2* | 2/2018 | Connor | A61B 5/0059 |
| 2001/0025917 | A1* | 10/2001 | Asada | G01L 5/226 250/221 |
| 2009/0092291 | A1* | 4/2009 | Nagasaka | G07C 9/37 382/115 |
| 2016/0313798 | A1* | 10/2016 | Connor | A61B 5/0488 |
| 2017/0001451 | A1* | 1/2017 | Bitoh | B41J 11/002 |
| 2017/0014075 | A1* | 1/2017 | Morimura | A61B 5/02422 |
| 2017/0060267 | A1* | 3/2017 | Piccionelli | G07F 17/3272 |
| 2018/0150687 | A1* | 5/2018 | Nada | G06K 9/00087 |
| 2018/0234415 | A1* | 8/2018 | Fukuda | G06F 21/32 |

OTHER PUBLICATIONS

Sakuma, K., Abrami, A., Blumrosen, G. et al. Wearable Nail Deformation Sensing for Behavioral and Biomechanical Monitoring and Human-Computer Interaction. Sci Rep 8, 18031 (2018). https://doi.org/10.1038/s41598-018-36834-x (Year: 2018).*

* cited by examiner

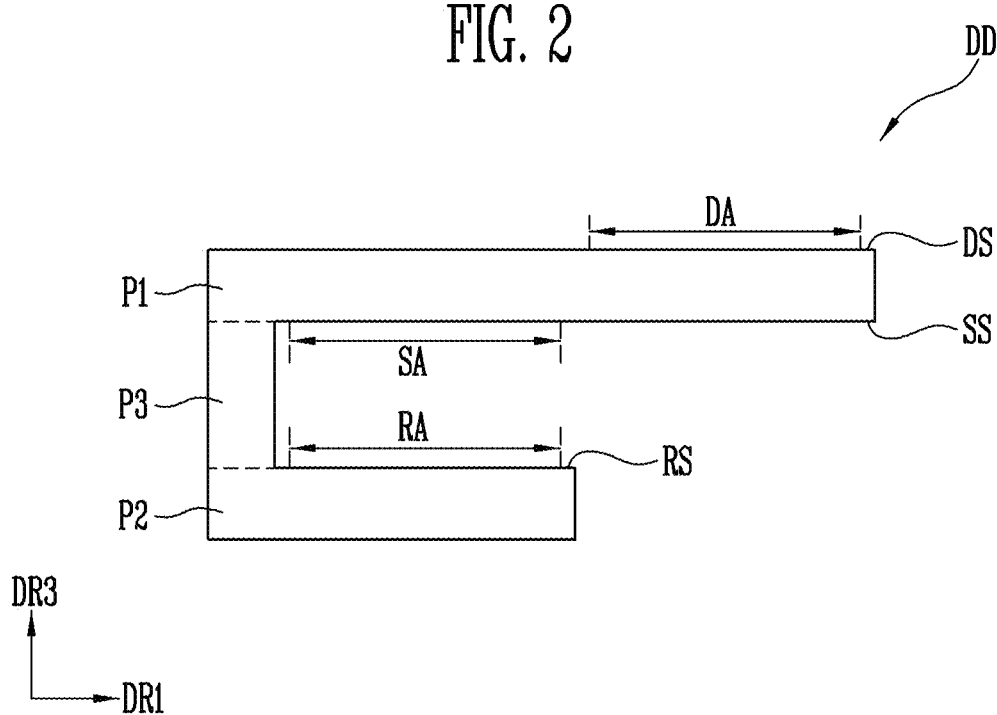
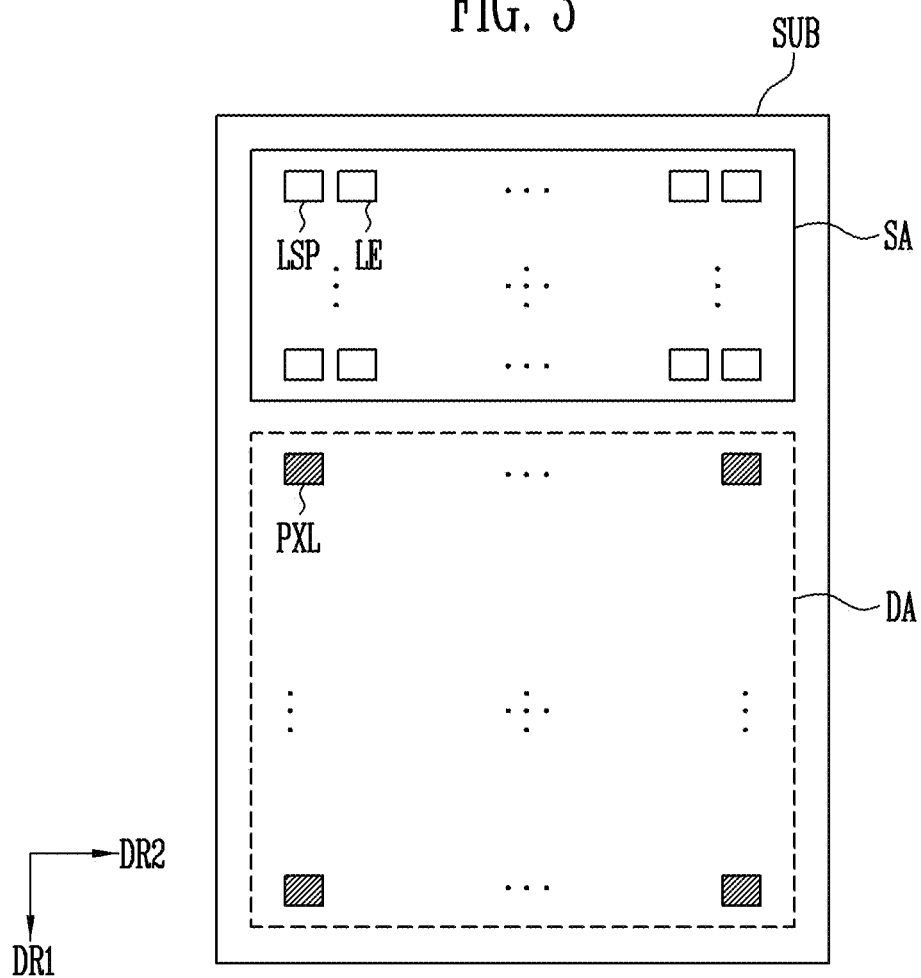

FIG. 8
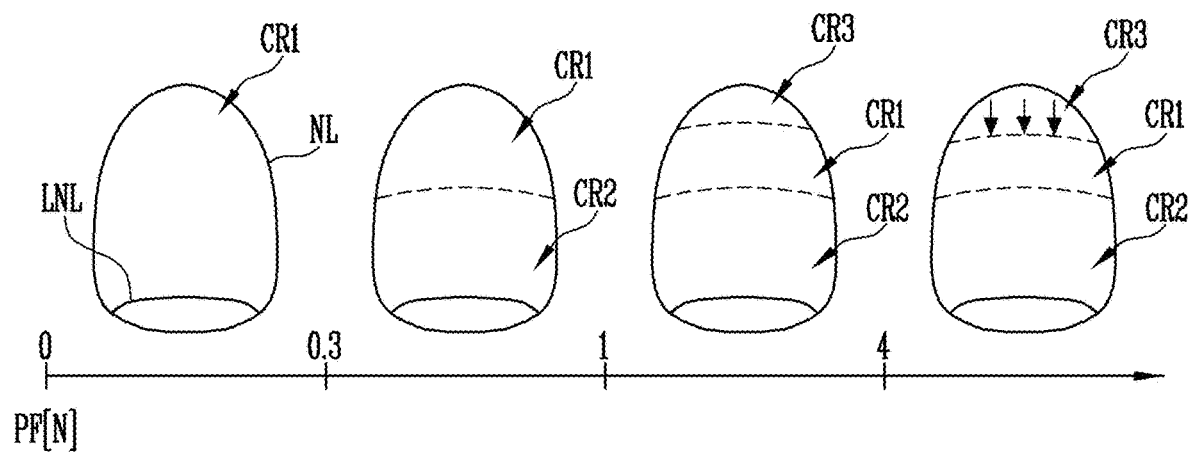
FIG. 9
[Flexion]
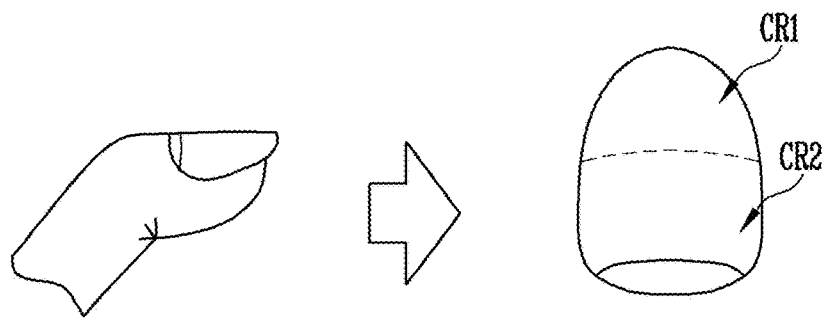
[Extension]
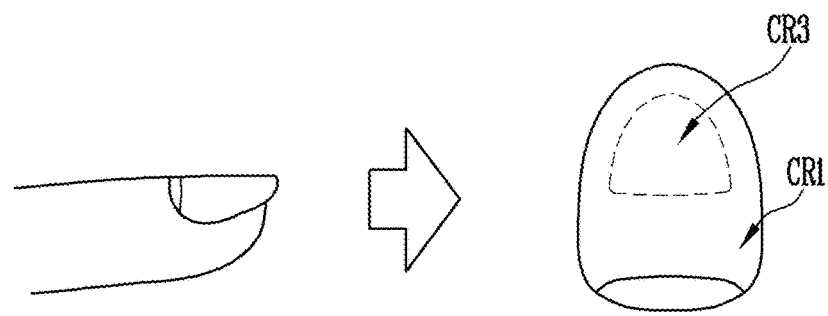

ELECTRONIC DEVICE

This application claims priority to Korean patent application No. 10-2018-0014204, filed on Feb. 5, 2018, and all the benefits accruing therefrom under 35 U.S.C. § 119, the content of which in its entirety is herein incorporated by reference.

BACKGROUND

1. Field

The disclosure relates to an electronic device.

2. Related Art

Recently, various electronic devices, which are typically worn directly on human bodies, have been developed. These devices are generally referred to as wearable devices.

In particular, such wearable devices may include a finger mounted electronic device (hereinafter, referred to as "FMD") that provides high-level convenience to users and thus may be used for various fields.

SUMMARY

Embodiments relate to an electronic device capable of sensing movement of a finger.

According to an embodiment of the disclosure, an electronic device to be mounted around a finger includes: a top part on which a nail of the finger is located; a bottom part disposed opposite to the top part, where a fingerprint surface of the finger is located on the bottom part; and a side part connecting the top part and the bottom part to each other, where the top part generates a nail image by image-picking up the nail, and senses a movement of the finger, based on the nail image.

In an embodiment, the top part may include: a substrate including a display area and a sensing area; display pixels disposed in the display area, where the display pixels may display an image through a display to surface that is a front surface of the top part; light emitting parts disposed in the sensing area, where the light emitting parts may emit light onto the nail through a sensing surface which is a back surface of the top part; and light sensing parts disposed in the sensing area, where the light sensing parts may sense reflected light through the sensing surface. In such an embodiment, the reflected light may be the light emitted from the light emitting parts and reflected by the nail.

In an embodiment, the display area and the sensing area may not overlap with each other.

In an embodiment, the display area and the sensing area may overlap with each other.

In an embodiment, each of the display pixels may include: a pixel semiconductor layer disposed on the substrate; a first gate electrode overlapping with the pixel semiconductor layer; and a first gate insulating layer disposed between the pixel semiconductor layer and the first gate electrode. In such an embodiment, each of the light sensing parts may include: a sensing semiconductor layer disposed on the first gate insulating layer; a second gate electrode overlapping with the sensing semiconductor layer; and a second gate insulating layer disposed between the sensing semiconductor layer and the second gate electrode.

In an embodiment, the second gate electrode may block external light to the sensing semiconductor layer through the display surface.

In an embodiment, the pixel semiconductor layer may include polycrystalline Si, and the sensing semiconductor layer may include amorphous to Si—Ge.

In an embodiment, a display element included in each of the display pixels may include: a first lower electrode including a transparent conductive layer and a reflective layer; an emitting layer disposed on the first lower electrode; and a first upper electrode disposed on the emitting layer. In such an embodiment, a display element included in each of the light emitting parts may include: a second lower electrode including the transparent conductive layer; an emitting layer disposed on the second lower electrode; and a second upper electrode disposed on the emitting layer.

In an embodiment, each of the first upper electrode and the second upper electrode may be a semi-transmissive reflective layer which reflects light in an infrared region.

In an embodiment, the display element included in each of the light emitting parts may further include a semi-transmissive reflective layer disposed on the second upper electrode, where the semi-transmissive reflective layer may overlap with the emitting layer. In such an embodiment, the semi-transmissive reflective layer may reflect light in an infrared region.

In an embodiment, the display element included in each of the light emitting parts may further include a capping layer disposed between the second upper electrode and the semi-transmissive reflective layer.

In an embodiment, the bottom part may generate a biometric image by image-picking up the fingerprint surface, and sense a heartbeat of a user, based on the biometric image.

In an embodiment, the bottom part may include: a substrate including an auxiliary area; and light sensing parts disposed in the auxiliary area, where the light sensing parts senses transmitted light through an auxiliary surface which is a front surface of the bottom part. In such an embodiment, the transmitted light may be the light emitted from the light emitting parts and transmitted through the finger.

In an embodiment, the light may be infrared light.

According to another embodiment of the disclosure, an electronic device to be mounted around a finger, includes: a light emitting part which emits light to a nail of the finger; a first light receiving part which generates a nail image by sensing the light emitted onto and reflected by the nail; and an image analyzer which senses a movement of the finger, based on the nail image.

In an embodiment, the electronic device may further include a second light receiving part which generates a biometric image by sensing the light emitted onto the nail and transmitted through the finger. In such an embodiment, the image analyzer may sense a heartbeat of a user, based on the biometric image.

In an embodiment, the image analyzer may generate pressure information, based on the nail image. In such an embodiment, the input information may represent a magnitude of a force with which the finger presses.

In an embodiment, the image analyzer may generate flexion information, based on the nail image. In such an embodiment, the flexion to information may represent whether the finger in a bent state.

In an embodiment, the image analyzer may generate direction information, based on the nail image. In such an embodiment, the direction information may represent a direction of a force with which the finger presses.

BRIEF DESCRIPTION OF THE DRAWINGS

The above and other features of the invention will become more apparent by describing in further detail exemplary embodiments thereof with reference to the accompanying drawings, in which:

FIG. 2 is a view illustrating a section of the electronic device according to an embodiment of the disclosure;

FIG. 3 is a view illustrating a top part of the electronic device shown in FIG. 2;

FIG. 8 is a view illustrating a driving method of the electronic device according to an embodiment of the disclosure;

FIG. 9 is a view illustrating a driving method of the electronic device according to an embodiment of the disclosure;

DETAILED DESCRIPTION

Figure 1A:
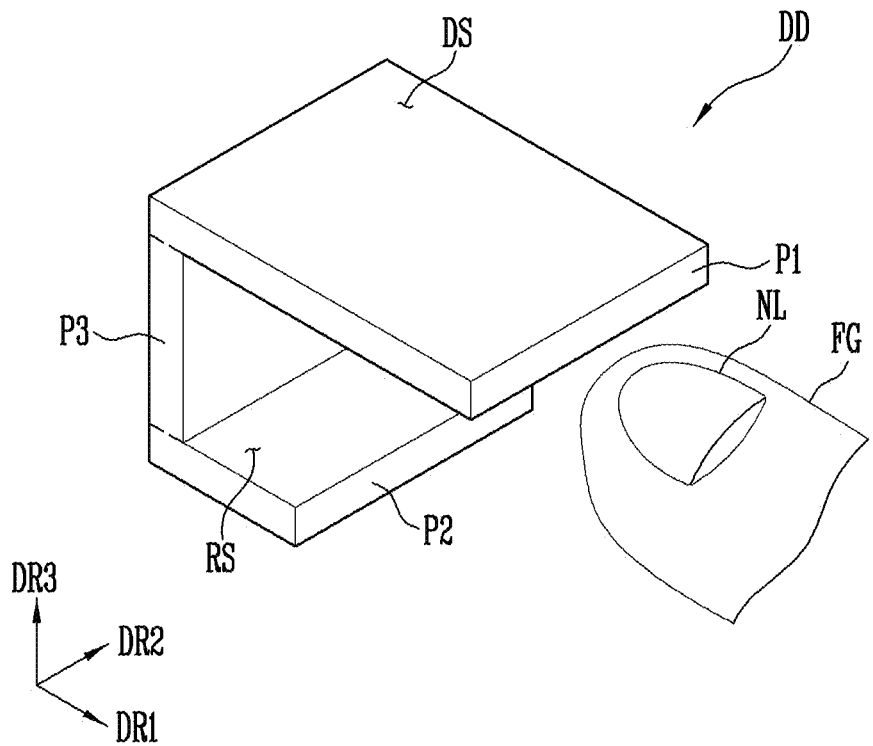
FIGS. 1A and 1B are views illustrating an electronic device according to an embodiment of the disclosure.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing to particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that, although the terms "first," "second," etc. may be used herein to describe one or more elements, these terms should not be construed as limiting such elements. These terms are only used to distinguish one element from another element. Thus, a first element could be alternately termed a second element without departing from the spirit and scope of the disclosure. Similarly, a second element could be alternately termed a first element. Singular forms of terms are intended to include the plural forms as well, unless the context clearly indicates otherwise.

Moreover, spatially relative terms, such as "beneath," "below," "lower," "above," "upper," and the like may be used herein for ease of description to describe one element's spatial relationship to another element(s) as illustrated in the drawings. It will be understood that the spatially relative terms are intended to encompass different orientations of the device in use or in to operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

In the entire specification, when an element is referred to as being "connected" or "coupled" to another element, it can be directly connected or coupled to the another element or be indirectly connected or coupled to the another element with one or more intervening elements interposed therebetween. Further, some of the elements that are not essential to the complete understanding of the disclosure are omitted for clarity. Also, like reference numerals refer to like elements throughout.

Hereinafter, exemplary embodiments of the disclosure will be to described in detail with reference to the accompanying drawings.

Herein, a front surface (or top surface) and a back surface (or bottom surface) of each member or unit described hereinbelow is distinguished by the third direction DR3. However, the first to third directions DR1, DR2, and DR3 illustrated in embodiments are merely illustrative, and the directions indicated by the first to third directions DR1, DR2, and DR3 are relative concepts, and may be changed into other directions. Hereinafter, first to third directions are directions respectively indicated by the first to third directions DR1, DR2 and DR3, and are designated by like reference numerals.

Hereinafter, embodiments of the invention will be described in detail with reference to the accompanying drawings.

Figure 1B:
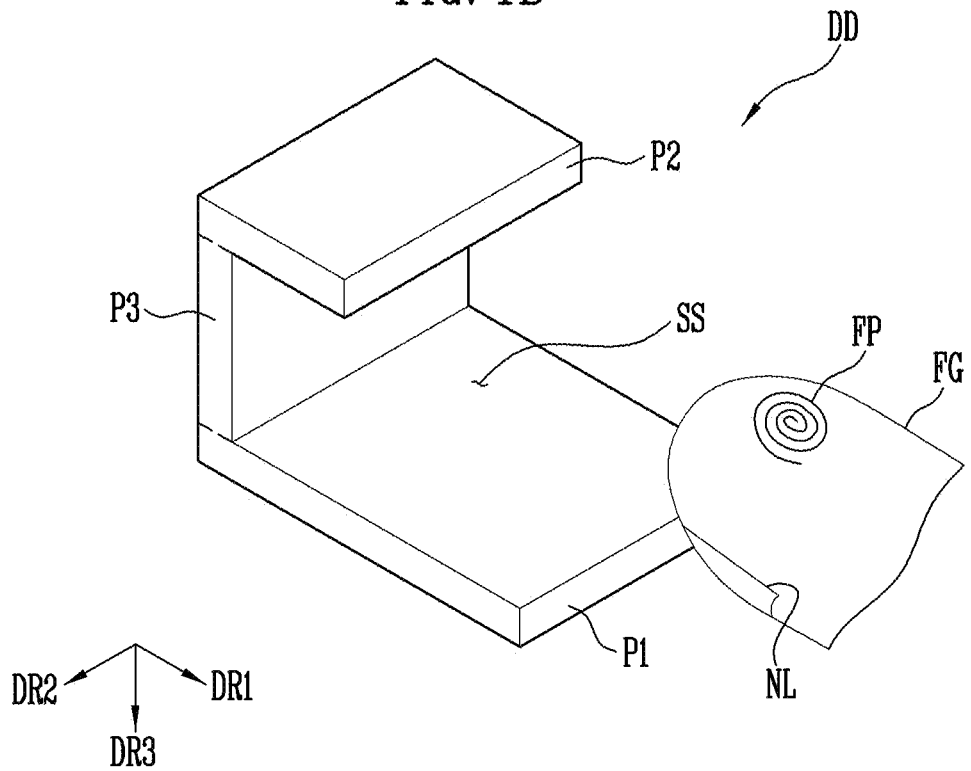

FIGS. 1A and 1B are views illustrating an electronic device according to an embodiment of the disclosure.

FIG. 1A illustrates a finger FG and an electronic device DD, which are viewed in a direction opposite to a third direction DR3, and FIG. 1B illustrates the finger FG and the electronic device DD, which are viewed in the third direction DR3.

Referring to FIGS. 1A and 1B, an embodiment of the electronic device DD may surround the finger FG. The electronic device DD may be attached or fixed to the finger FG.

In one embodiment, for example, the electronic device DD may have a curved shape to surround the finger FG. The electronic device DD may include a top part P1, a bottom part P2, and a side part P3.

When the finger FG is fixed or attached to the electronic device DD, the top part P1 of the electronic device DD may be located on a nail NL of the finger FG, and the bottom part P2 of the electronic device DD may be located under a fingerprint surface FP of the finger FG.

The side part P3 may connect the top part P1 and the bottom part P2 to each other. In such an embodiment, the side part P3 may be a component for supporting the top part P1 and the bottom part P2.

However, the disclosure is not limited thereto. In some embodiments, the electronic device DD may be implemented in one of various shapes which allow the object of the disclosure to achieve.

The electronic device DD may include a display surface DS, a sensing surface SS, and an auxiliary surface RS.

The display surface DS may mean a front surface (or a top surface) of the top part P1, the sensing surface SS may mean a back surface (or a bottom surface) of the top part P1, and the auxiliary surface RS may mean a front surface (or a top surface) of the bottom part P2. In some embodiments, the sensing surface SS and the auxiliary surface RS may be disposed to face each other.

The display surface DS, the sensing surface SS and the auxiliary surface RS may be a surface parallel to a plane defined by a first direction DR1 and a second direction DR2.

An embodiment, in which the display surface DS, the sensing surface SS and the auxiliary surface RS of the electronic device DD are planar to surfaces, is illustrated in FIGS. 1A and 1B, but the disclosure is not limited thereto. In some alternative embodiments, the display surface DS, the sensing surface SS and the auxiliary surface RS may be curved or stereoscopic surfaces. The stereoscopic display surface DS includes a plurality of display areas indicating different directions, and may include, for example, a polygonal column-shaped display surface.

In such an embodiment, the electronic device DD may be implemented as a rigid display device. However, the disclosure is not limited thereto, and alternatively, the electronic device DD may be implemented as a flexible display device.

In such an embodiment, the electronic device DD may display an image through the display surface DS.

In one embodiment, for example, the electronic device DD may be a light emitting display device. In such an embodiment, the electronic device DD may be, for example, an organic light emitting display device or a quantum dot light emitting display device. In such an embodiment, an emitting layer of the quantum dot light emitting display device may include a quantum dot, a quantum rod, and the like. Hereinafter, for convenience of description, embodiments where the electronic device DD is the organic light emitting display device will be described in detail.

The electronic device DD may generate a nail image representing an outer surface of the nail NL by image-picking up the nail NL (i.e., picking-up an image of the nail NL) through the sensing surface SS.

The electronic device DD may sense a movement of the finger FG, based on the nail image. Thus, a user moves the finger FG, to provide an input to the electronic device DD.

In some embodiment, the electronic device DD may emit light through the sensing surface SS. The electronic device DD may image-pick up the nail NL by receiving light reflected by the nail NL. The electronic device DD may generate a nail image, based on the reflected light. In one embodiment, for example, the light may be infrared light.

In an embodiment, the electronic device DD may sense a heartbeat of the user through the auxiliary surface RS. In such an embodiment, the electronic device DD may acquire biometric information (e.g., heartbeat information) of the user by image-picking up the fingerprint surface FP through the auxiliary surface RS. In some embodiments, the electronic device DD may image-pick up the fingerprint surface FP by receiving light transmitted through the finger FG. The electronic device DD may generate biometric information (e.g., heartbeat information) of the user, based on the transmitted light.

The electronic device DD may sense a heartbeat of the user, based on the biometric information of the user.

FIG. 2 is a view illustrating a section of the electronic device DD according to an embodiment of the disclosure.

Referring to FIG. 2, in an embodiment, the display surface DS may include a display area DA in which an image is displayed. In the display surface DS, an area except the display area DA may be defined as a non-to display area.

The sensing surface SS may include a sensing area for image-picking up the nail NL.

In an embodiment, as shown in FIG. 2, the sensing area SA and the display area DA may not overlap with each other.

The auxiliary surface RS may include an auxiliary area for image-picking up the fingerprint surface FP.

In an embodiment, as shown in FIG. 2, the auxiliary area RA and the sensing area SA may face each other. The auxiliary area RA and the sensing area SA may overlap with each other.

Although not shown in FIG. 2, the top part P1 may include a substrate, display pixels, light sensing parts, and light emitting parts. The bottom part P2 may include a substrate and light sensing parts.

FIG. 3 is a view illustrating the top part P1 of the electronic device shown in FIG. 2.

For convenience of description, the sensing area SA is indicated by a solid line, and the display area DA is indicated by a dotted line. Herein, the solid line and the dotted line may be imaginary lines.

The sensing area SA and the display area DA may not overlap with each other.

The top part P1 may include a substrate SUB, display pixels PXL, light sensing parts LSP, and light emitting parts LE.

The substrate SUB may include the display area DA and the to sensing area SA.

The display pixels PXL, the light sensing parts LSP and the light emitting parts LE may be defined or formed on the substrate SUB.

In an embodiment, each of the display pixels PXL may emit light. In such an embodiment, the display pixel PXL may display an image through the display surface DS.

The display pixel PXL may be disposed in the display area DA. In some embodiments, the display pixels PXL may be arranged substantially in a matrix form.

Although not shown in FIG. 3, the top part P1 may further include driving lines connected to the display pixels PXL and a driver for applying driving signals to the driving lines.

In an embodiment, each of the light emitting parts LE may emit light. In such an embodiment, the light emitting parts LE may emit light onto the nail NL.

The light emitting parts LE may be disposed in the sensing area SA. In some embodiments, the light emitting parts LE may be arranged substantially in a matrix form.

Although not shown in FIG. 3, the top part P1 may further include emission driving lines connected to the light emitting parts LE and an emission driver for applying emission driving signals to the emission driving lines.

In an embodiment, each of the light sensing parts LSP may receive light. In such an embodiment, the light sensing parts LSP may sense to reflected light through the sensing surface SS.

The light sensing parts LSP may be disposed in the sensing area SA. In some embodiments, the light sensing parts LSP may be arranged in a matrix structure.

Although not shown in FIG. 3, the top part P1 may further include sensing driving lines connected to the light sensing parts LSP and a sensing driver for applying sensing driving signals to the sensing driving lines.

In an embodiment, as shown in FIG. 3, the light emitting parts LE and the light sensing parts LSP may be located adjacent to each other, or disposed alternately with each other.

In an embodiment, as shown in FIG. 3, the light emitting parts LE and the light sensing parts LSP may correspond one-to-one to each other, but the disclosure is not limited thereto. In some embodiments, the light emitting parts LE and the light sensing parts LSP may correspond n-to-m (n and m are natural numbers of 2 or more), 1-to-m, or n-to-1 to each other, or may not correspond to each other.

In an embodiment, as shown in FIG. 3, the light emitting parts LE, and the light sensing parts LSP have a same size as each other, but the disclosure is not limited thereto. In some embodiments, the display pixels PXL, the size of the light emitting parts LE and the size of the light sensing parts LSP may be variously modified to an extend that allows the object of the disclosure to be achieved.

Figure 4:
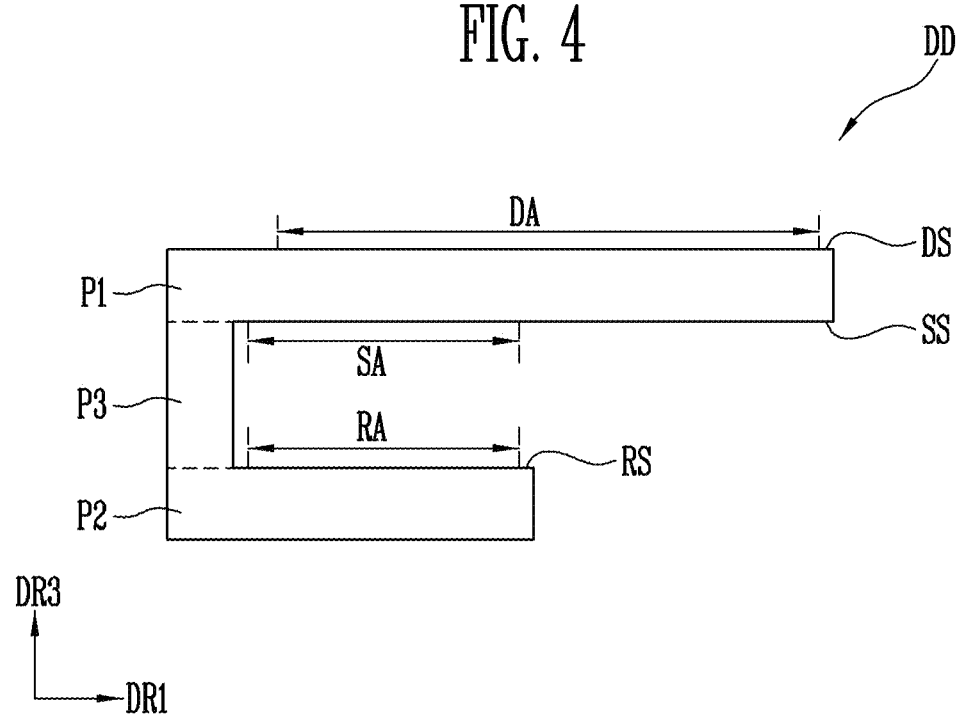
FIG. 4 is a view illustrating a section of the electronic device according to alternative embodiment of the disclosure.

FIG. 4 is a view illustrating a section of the electronic device DD to according to an alternative embodiment of the disclosure. Hereinafter, features of the electronic device DD of FIG. 4 that are different from those of the embodiments described above with reference to FIG. 2 will be mainly described for convenience of description. The embodiment shown in FIG. 4 may be substantially the same as that shown in FIG. 2, except that the sensing area SA and the display area DA may overlap with each other. In such an embodiment, as shown in FIG. 4, the sensing area SA may partially overlap with the display area DA. In some embodiments, unlike the embodiment shown in FIG. 4, the sensing area SA may entirely overlap with the display area DA.

Figure 5:
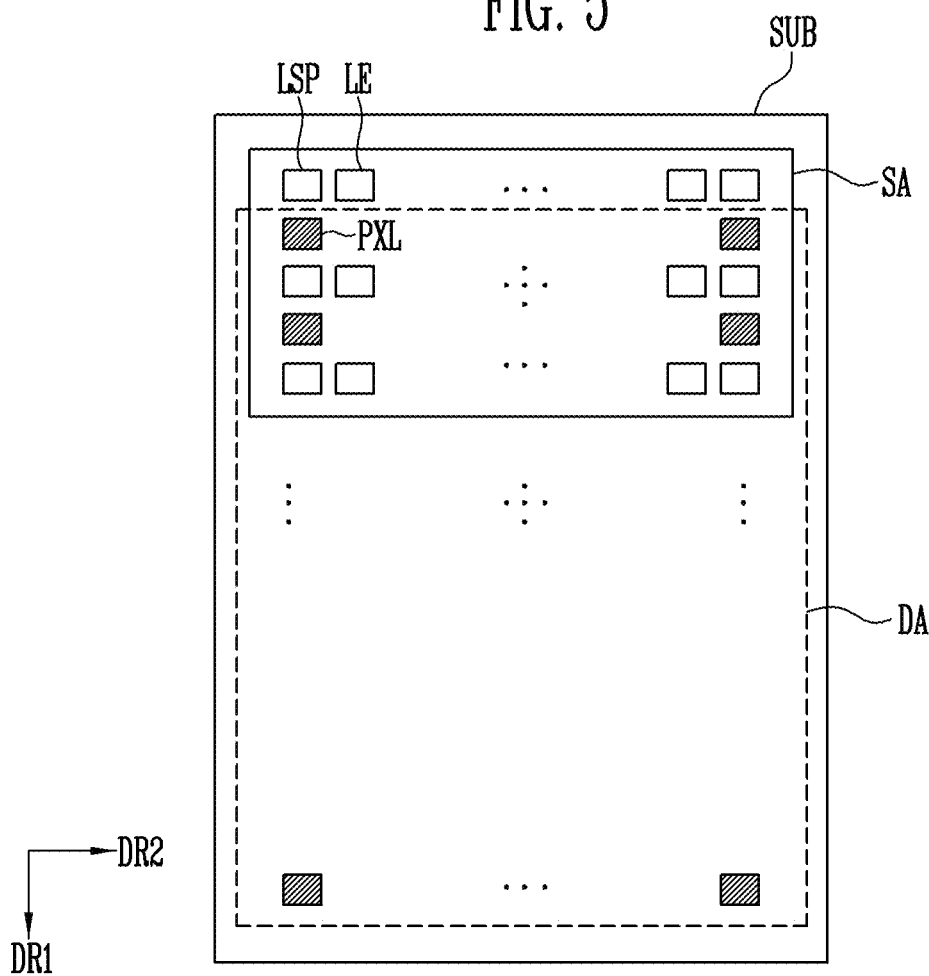
FIG. 5 is a view illustrating a top part of the electronic device shown in FIG. 4.

FIG. 5 is a view illustrating a top part P1 of the electronic device DD shown in FIG. 4. Hereinafter, features of a top part P1 of the electronic device DD of FIG. 5 that are different from those of the embodiment described in FIG. 3 will be mainly described for convenience of description. The embodiment shown in FIG. 5 may be substantially the same as that shown in FIG. 3, except that the display pixels PXL, the light emitting parts LE and the light sensing parts LSP may be arranged substantially in in a matrix form in the area in which the display area DA and the sensing area SA overlap with each other.

Figure 6:
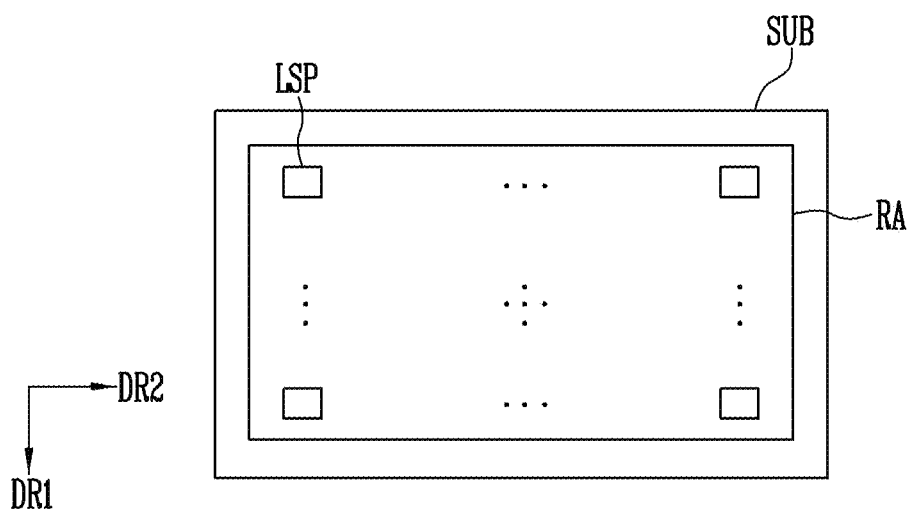
FIG. 6 is a view illustrating a bottom part of the electronic device according to an embodiment of the disclosure.

FIG. 6 is a view illustrating a bottom part P2 of the electronic device DD according to an embodiment of the disclosure. For convenience of description, the auxiliary area RA is indicated by a solid line.

The bottom part P2 may include a substrate SUB and light sensing parts LSP.

In an embodiment, the light sensing parts LSP may be defined or formed on the substrate SUB. Each of the light sensing parts LSP may receive light. In such an embodiment, the light sensing parts LSP may sense transmitted light through the auxiliary surface RS. The light sensing parts LSP may be disposed in the auxiliary area RA. In some embodiments, the light sensing parts LSP may be arranged in a matrix structure.

Although not shown in FIG. 5, the bottom part P2 may further include sensing driving lines connected to the light sensing parts LSP and a sensing driver for applying sensing driving signals to the sensing driving lines.

In some embodiments, the light sensing parts LSP shown in FIG. 6 may be substantially the same as the light sensing parts LSP shown in FIGS. 3 and 5.

Figure 7:
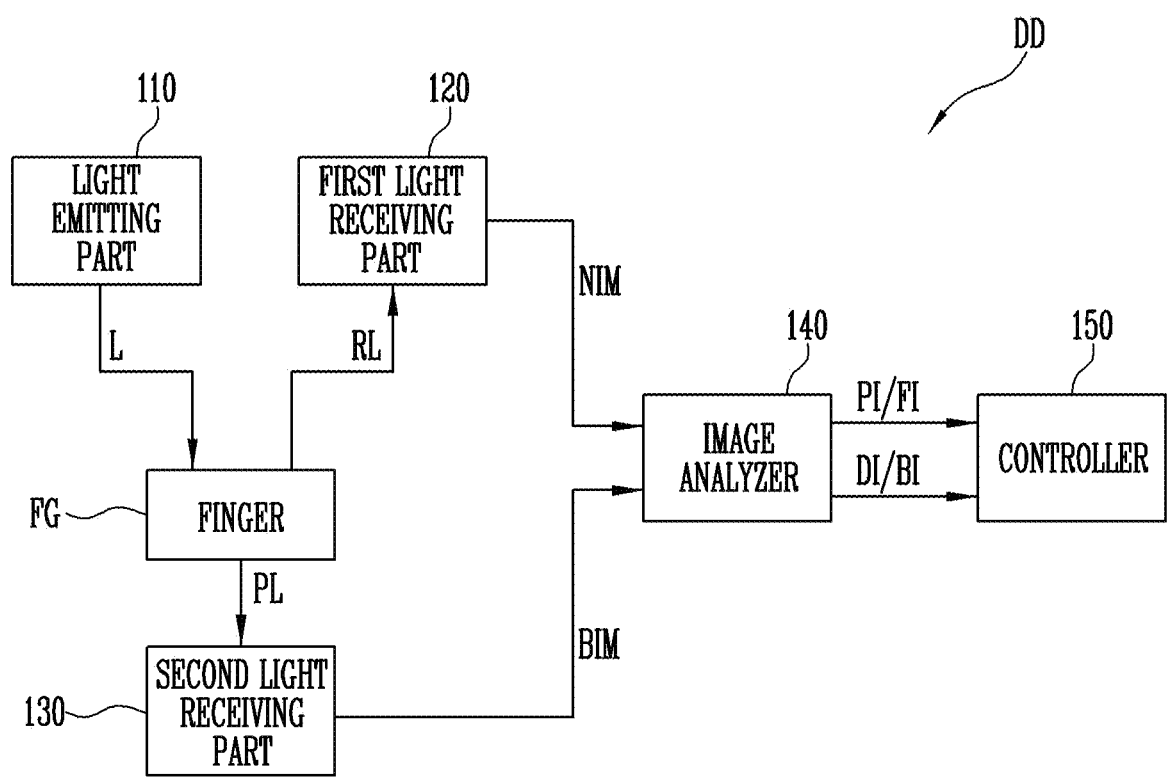
FIG. 7 is a view briefly illustrating an electronic device according to an embodiment of the disclosure.

FIG. 7 is a view briefly illustrating an electronic device DD according to an embodiment of the disclosure.

Referring to FIGS. 1 to 7, an embodiment of the electronic device DD may include a light emitting part 110, a first light receiving part 120, a second light receiving part 130, an image analyzer 140, and a controller 150.

The light emitting part 110 may emit light L onto the nail NL through the sensing surface SS. The light L may be reflected by the nail NL, or be transmitted through the finger FG. In one embodiment, for example, the light emitting part 110 may emit light L onto the sensing area SA. The light emitting part 110 may include light emitting parts LE that emit the light L. In one embodiment, for example, the light L may be infrared light.

The first light receiving part 120 may receive a reflected light RL through the sensing surface SS. Here, the reflected light RL may mean the light L reflected by the nail NL. In one embodiment, For example, the first light receiving part 120 may sense the reflected light RL in the sensing area. The first light receiving part 120 may include light sensing parts LSP included in the top part P1. The first light receiving part 120 may generate a nail image NIM, based on the reflected light RL. The first receiving part 120 may transmit the nail image NIM to the image analyzer 140.

The second light receiving part 130 may receive transmitted light PL through the auxiliary surface RS. Here, the transmitted light PL may mean light L transmitted through the finger FG. In one embodiment, for example, the second light receiving part 130 may sense the transmitted light PL in the auxiliary area RA. The second light receiving part 130 may include light sensing parts LSP included in the bottom part P2. The second light receiving part 130 may generate a biometric image BIM, based on the transmitted light PL. The second light receiving part 130 may transmit the biometric image BIM to the image analyzer 140.

The image analyzer 140 may receive the nail image NIM from the first light receiving part 120, and receive the biometric image BIM from the second light receiving part 130.

The image analyzer 140 may sense a movement of the finger FG, based on the nail image NIM.

In such an embodiment, the image analyzer 140 may sense a to heartbeat of the user, based on the nail image NIM or the biometric image BIM. In general, the flow of blood may be changed depending on cardiac impulse, and the color of the nail or the color of the fingerprint surface may be changed depending on the flow of blood. The nail image NIM may include a change in color of the nail, and the biometric image BIM may include a change in color of the fingerprint surface. Thus, in such an embodiment, image analyzer 140 may effectively sense the heartbeat of the user, based on the nail image NIM or the biometric image BIM.

In some embodiments, the image analyzer 140 may generate pressure information PI, based on the nail image NIM. The pressure information PI may represent the magnitude of a force with which the finger FG presses. This will be described later in greater detail with reference to FIG. 8. The image analyzer 140 may transmit the pressure information PI to the controller 150.

The image analyzer may generate flexion information FI, based on the nail image NIM. The flexion information Fl may represent whether the finger FG is in a bent state or not. This will be described later in greater detail with reference to FIG. 9. The image analyzer 140 may transmit the flexion information to the controller 150.

The image analyzer 140 may generate direction information DI, based on the nail image NIM. The direction information DI may represent the direction of a force with which the finger FG presses. This will be described later in greater detail with reference to FIG. 10. The image analyzer 140 may to transmit the direction information to the controller 150.

The image analyzer 140 may generate biometric information BI, based on the nail image NIM or the biometric image BIM. In one embodiment, for example, the biometric information may include heartbeat information of the user. The image analyzer 140 may transmit the biometric information BI to the controller 150.

The controller 150 may control overall operation of the electronic device DD. In one embodiment, for example, the controller 150 may control operations of the light emitting part 110, the first light receiving part 120, the second light receiving part 130, and the image analyzer 140.

In one embodiment, for example, the controller 150 may control an operation of the electronic device DD, based on at least one of the pressure information PI, the flexion information FI, the direction information DI, and the biometric information BI.

FIG. 8 is a view illustrating a driving method of the electronic device DD according to an embodiment of the disclosure.

Referring to FIGS. 1 to 8, an embodiment of the electronic device DD may generate pressure information PI, based on a nail image NIM.

A nail image NIM according to a force with which a finger FG presses, i.e., a finger pressure PF, is exemplarily illustrated in FIG. 8.

For convenience of description, description of a half-moon part LNL of a nail NL will be omitted below. In FIG. 8, for convenience of illustration, it is illustrated that parts of the nail NL are clearly distinguished from one to another, but the disclosure is not limited thereto. In one embodiment, for example, the color of each part of the nail NL may be gradually changed, and such parts may be arbitrarily distinguished from one another.

When the finger pressure PF is in a range from zero (0) newton (N) to 0.3 N, the nail image NIM may show the nail NL having a first color CR1. In one embodiment, for example, the first color CR1 may represent apricot or pink.

When the finger pressure PF is in a range from 0.3 N to 1 N, the nail image NIM may show the nail NL having the first color CR1 and a second color CR2. As shown in FIG. 8, a first part of the nail NL may have the first color CR1, and a second part of the nail NL may have the second color CR2. The first part may be located at an upper end of the nail NL, and the second part may be located at a lower end of the nail NL. In one embodiment, for example, the second color CR2 may represent red or reddish brown.

When the finger pressure PF is in a range from 1 N to 4 N, the nail image NIM may show the nail NL having the first color CR1, the second color CR2, and a third color CR3. As shown in FIG. 8, a first part of the nail NL may have the first color CR1, a second part of the nail NL may have the second color CR2, and a third part of the nail NL may have the third color CR3. The first part may be located at a middle end of the nail NL, the second part is located at a lower end of the nail NL, and the third part may be located at an upper end of the nail NL. In one embodiment, for example, the third color may represent bright pink or white.

When the finger pressure PF is 4 N or greater, the nail image NIM may show the nail NL having the first color, the second color, and the third color CR3. As shown in FIG. 8, a first part of the nail NL may have the first color CR1, a second part of the nail NL may have the second color CR2, and a third part of the nail NL may have the third color CR3. The first part may be located at a middle end of the nail NL, the second part is located at a lower end of the nail NL, and the third part may be located at an upper end of the nail NL. In such an embodiment, the third part may be wider than that when the finger pressure PF is in a range from 1 N to 4 N.

FIG. 9 is a view illustrating a driving method of the electronic device DD according to an embodiment of the disclosure.

Referring to FIGS. 1 to 9, an embodiment of the electronic device DD may generate flexion information FI, based on a nail image NIM.

A nail image NIM according to a flexion state and an extension state of a finger FG is exemplarily illustrated in FIG. 9.

In FIG. 9, it is illustrated that parts of a nail NL are clearly distinguished from one another, but the disclosure is not limited thereto. In one embodiment, for example, the color of each part of the nail NL may be gradually changed, and such parts may be arbitrarily distinguished from one another.

When the finger FG is in the flexion state, the nail image NIM may show the nail NL having a first color CR1 and a second color CR2. As shown in FIG. 9, a first part of the nail NL may have the first color CR1, and a second part of the nail NL may have the second color CR2. In one to embodiment, for example, the first part of the nail NL may be located at an upper end of the nail NL, and the second part may be located at a lower end of the nail NL.

When the finger FG is in the extension state, the nail image NIM may show the nail NL having the first color CR1 and a third color CR3. As shown in FIG. 9, a first part of the nail NL may have the first color CR1, and a third part of the nail NL may have the third color CR3. In one embodiment, for example, the third part of the nail NL may be located at a middle end of the nail NL, and the first part may surround the third part.

Figure 10:
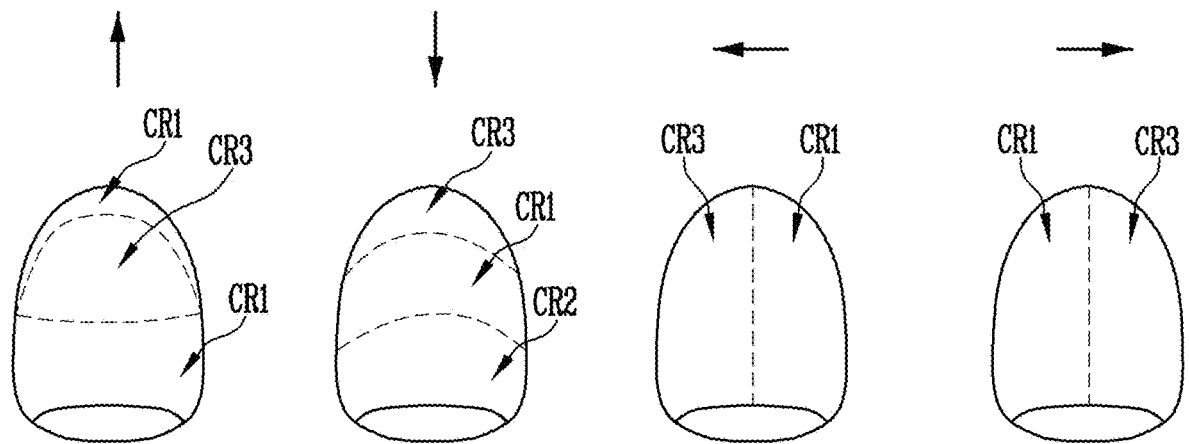
FIG. 10 is a view illustrating a driving method of the electronic device according to an embodiment of the disclosure.

FIG. 10 is a view illustrating a driving method of the electronic device DD according to an embodiment of the disclosure.

Referring to FIGS. 1 to 10, an embodiment of the electronic device DD may generate direction information DI, based on a nail image NIM.

A nail image NIM according to a force with which a finger FG presses, i.e., the direction of a finger pressure PF, is exemplarily illustrated in FIG. 10.

In FIG. 10, it is illustrated that parts of a nail NL are clearly distinguished from one another, but the disclosure is not limited thereto. In one embodiment, for example, the color of each part of a nail NL may be gradually changed, and such parts may be arbitrarily distinguished from one another.

When the direction of the finger pressure PF is an upper direction, the nail image NIM may show the nail NL having a first color CR1 and a third color CR3. As shown in FIG. 10, a first part of the nail NL may have the to first color CR1, and a third part of the nail NL may have the third color CR3. In one embodiment, for example, the first part may be located at upper and lower ends of the nail NL, and the third part may be located at a middle end of the nail NL.

When the direction of the finger pressure PF is a lower direction, the nail image NIM may show the nail NL having the first color CR1, a second color CR2, and the third color CR3. As shown in FIG. 10, a first part of the nail NL may have the first color CR1, a second part of the nail NL may have the second color CR2, and a third part of the nail NL may have the third color CR3. In one embodiment, for example, the first part may be located at a middle end of the nail NL, the second part may be located at a lower end of the nail NL, and the third part may be located at an upper end of the nail NL.

When the direction of the finger pressure PF is a left direction, the nail image NIM may show the nail having the first color CR1 and the third color CR3. As shown in FIG. 10, a first part of the nail NL may have the first color CR1, and a third part of the nail NL may have the third color CR3. In one embodiment, for example, the first part may be located at a right end of the nail NL, and the third part may be located at a left end of the nail NL.

When the direction of the finger pressure PF is a right direction, the nail image NIM may show the nail NL having the first color and the third color CR3. As shown in FIG. 10, a first part of the nail NL may have the first color CR1, and a second part of the nail NL may have the third color CR3. In one embodiment, for example, the first part may be located at a left end of the to nail NL, and the third part may be located at a right end of the nail NL.

Figure 11:
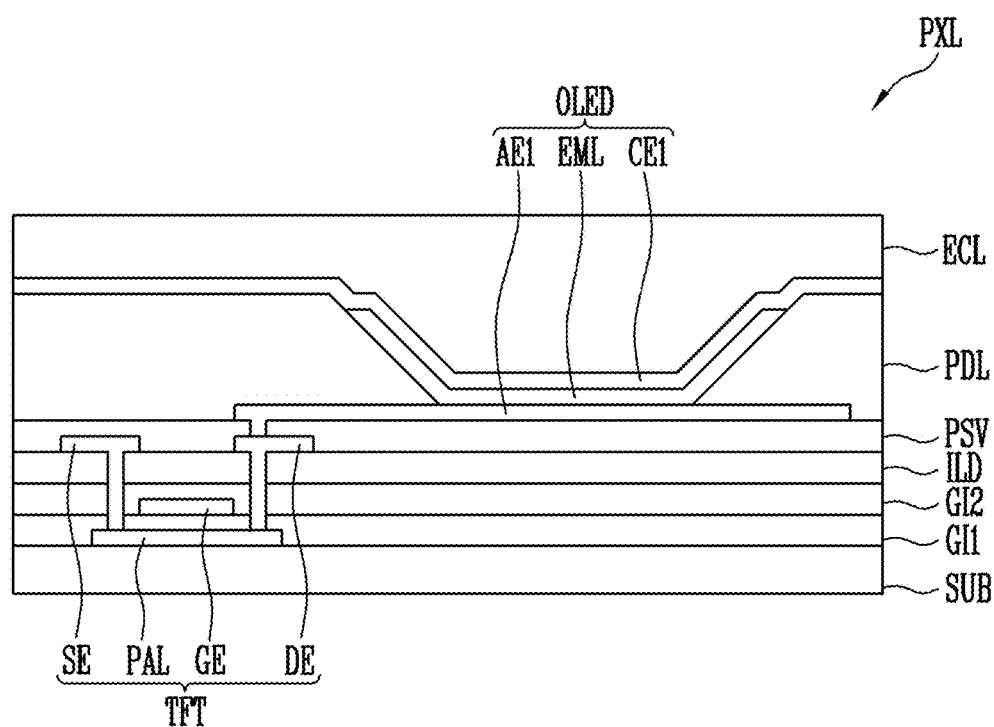
FIG. 11 is a view illustrating a section of a display pixel according to an embodiment of the disclosure.

FIG. 11 is a view illustrating a section of a display pixel PXL according to an embodiment of the disclosure. A section of the display pixel PXL and the substrate SUB, which are included in the top part P1, is illustrated in FIG. 11.

Referring to FIGS. 1 to 11, an embodiment of the display pixel PXL may include a thin film transistor TFT disposed on the substrate SUB, and a display element OLED connected to the thin film transistor TFT. In one embodiment, for example, the display element OLED may be an organic light emitting element.

The substrate SUB may include a transparent insulating material to enable light to be transmitted therethrough. A surface exposed to the outside of the substrate SUB, i.e., an outer surface of the substrate SUB, may be the sensing surface SS.

In such an embodiment, the substrate SUB may be a flexible substrate. The flexible substrate may include a film substrate and a plastic substrate, which include a polymer organic material. In such an embodiment, the flexible substrate may include fiber glass reinforced plastic ("FRP"). The material included in the substrate SUB may have resistance (or heat resistance) against high processing temperature in a manufacturing process of the display device.

The thin film transistor TFT may be disposed on the substrate SUB. The thin film transistor TFT may be connected to a gate line (not shown) to and a data line (not shown). The thin film transistor TFT may include a pixel semiconductor layer PAL, a gate electrode GE, a source electrode SE, and a drain electrode DE.

The pixel semiconductor layer PAL may be disposed on the substrate SUB.

In one embodiment, for example, the pixel semiconductor layer PAL may include at least one of amorphous Si, polycrystalline Si, oxide semiconductor, and organic semiconductor. In the pixel semiconductor layer PAL, regions connected to the source electrode SE and the drain electrode DE may be source and drain regions doped or injected with an impurity. In the pixel semiconductor layer PAL a region between the source region and the drain region may be a channel region.

A first gate insulating layer GI1 may be disposed over the pixel semiconductor layer PAL. The first gate insulating layer GI1 covers the pixel semiconductor layer PAL, and may insulate the pixel semiconductor layer PAL and the gate electrode GE from each other.

The first gate insulating layer GI1 may include at least one of an organic insulating material and an inorganic insulating material. In one embodiment, for example, the first gate insulating layer GI1 may include at least one of silicon oxide and silicon nitride.

The gate electrode GE may be disposed on the first gate insulating layer GI1. The gate electrode GE may include a low-resistance conductive material, and overlap with the pixel semiconductor layer PAL.

A second gate insulating layer GI2 may be disposed over the gate electrode GE. The second gate insulating layer GI2 may include at least one of an organic insulating material and an inorganic insulating material. In one embodiment, for example, the second gate insulating layer GI2 may include at least one of silicon oxide and silicon nitride.

An interlayer insulating layer ILD may be disposed on the second gate insulating layer GI2. The interlayer insulating layer ILD may include at least one of an organic insulating material and an inorganic insulating material. In one embodiment, for example, the interlayer insulating layer ILD may include at least one of silicon oxide and silicon nitride.

The interlayer insulating layer ILD may insulate the gate electrode GE from the source electrode SE and the drain electrode DE.

In such an embodiment, the source region and the drain region of the pixel semiconductor layer PAL may be exposed via contact holes defined through the first gate insulating layer GI1, the second gate insulating layer GI2, and the interlayer insulating layer ILD.

The source electrode SE and the drain electrode DE may be disposed on the interlayer insulating layer ILD to be spaced apart from each other. The source electrode SE and the drain electrode DE may include a low-resistance conductive material.

One end of the source electrode SE may be connected to the data line. The other end of the source electrode SE may be connected to the source region through one of the contact holes.

One end of the drain electrode DE may be connected to the drain region through another of the contact holes. The other end of the drain electrode DE may be connected to the display element OLED.

A protective layer PSV may be disposed over the thin film transistor TFT. The protective layer PSV may cover the thin film transistor TFT. A portion of the protective layer PSV may be removed, to expose one of the source electrode SE and the drain electrode DE, e.g., the drain electrode DE.

The protective layer PSV may have a single-layer structure or a multi-layer structure. In one embodiment, for example, the protective layer PSV may include an inorganic protective layer and an organic protective layer disposed on the inorganic protective layer. In such an embodiment, the inorganic protective layer may include at least one of silicon oxide and silicon nitride. In such an embodiment, the organic protective layer may include one of acryl, polyimide ("PI"), polyamide ("PA"), and benzocyclobutene ("BCB"). In such an embodiment, where the organic protective layer is transparent and flexible, the organic protective layer may be a planarization layer which reduces and planarizes winding of a lower structure.

The display element OLED may be disposed on the protective layer PSV. The display element OLED may include a first lower electrode AE1 connected to the thin film transistor TFT, an emitting layer EML provided on the first lower electrode AE1, and a first upper electrode CE1 provided on the emitting layer EML. In an embodiment, one of the first lower electrode AE1 and the first upper electrode CE1 may be an anode electrode, and the other of to the first lower electrode AE1 and the first upper electrode CE1 may be a cathode electrode. In one embodiment, for example, the first lower electrode AE1 may be an anode electrode, and the first upper electrode CE1 may be a cathode electrode.

In an embodiment, at least one of the first lower electrode AE1 and the first upper electrode CE1 may be a transmissive electrode. In one embodiment, for example, when the display element OLED is a bottom-emission type organic light emitting element, the first lower electrode AE1 may be a transmissive electrode, and the first upper electrode CE1 may be a reflective electrode. In an embodiment, where the display element OLED is a top-emission type organic light emitting element, the first lower electrode AE1 may be a reflective electrode, and the first upper electrode CE1 may be a transmissive electrode. In an embodiment, where the display element OLED is a dual-emission type organic light emitting element, both of the first lower electrode AE1 and the first upper electrode CE1 may be transmissive electrodes. In such an embodiment, where the display element OLED is the dual-emission type organic light emitting element, and the first lower electrode AE1 may be an anode electrode, for example.

The first lower electrode AE1 may be disposed on the protective layer PSV. The first lower electrode AE1 may have a multi-layered structure. In one embodiment, for example, the first lower electrode AE1 may have a structure in which a transparent conductive layer (not shown) capable of allowing light to be transmitted therethrough, a reflective layer (not shown) to capable of reflecting light, and a transparent conductive layer (not shown) are sequentially stacked. In such an embodiment, the reflective layer may be disposed between the transparent conductive layers. The transparent conductive layer located under the reflective layer may be connected to the drain electrode DE.

The transparent conductive layer may include a transparent conductive oxide. In one embodiment, for example, the transparent conductive layer may include at least one transparent conductive oxide among indium tin oxide ("ITO"), indium zinc oxide ("IZO"), aluminum zinc oxide ("AZO"), gallium doped zinc oxide ("GZO"), zinc tin oxide ("ZTO"), gallium tin oxide ("GTO"), and fluorine doped tin oxide ("FTO").

The reflective layer may include a material capable of reflecting light. In one embodiment, for example, the reflective layer may include at least one of aluminum (Al), silver (Ag), chromium (Cr), molybdenum (Mo), platinum (Pt), nickel (Ni), and an alloy thereof.

A pixel defining layer PDL may be disposed over the first lower electrode AE1. The pixel defining layer PDL may be disposed between pixel areas, and expose the first lower electrode AE1. In an embodiment, the pixel defining layer PDL may overlap with an edge portion of the first lower electrode AE1.

The pixel defining layer PDL may include an organic insulating material.

The emitting layer EML may be disposed on the first upper to electrode CE1. The first upper electrode CE1 may be a semi-transmissive reflective layer. In some embodiments, the first upper electrode CE1 may be a thin metal layer having a thickness thin enough to allow light to transmit therethrough. The first upper electrode CE1 may allow a portion of the light to be transmitted therethrough, and reflect a remaining portion of the light. In one embodiment, for example, the semi-transmissive reflective layer may allow light in ultraviolet and visible regions to be transmitted therethrough, and reflect light in an infrared region.

The first upper electrode CE1 may include a material having a work function lower than that of the transparent conductive layer. In one embodiment, for example, the first upper electrode CE1 may include at least one of molybdenum (Mo), tungsten (W), silver (Ag), magnesium (Mg), aluminum (Al), platinum (Pt), palladium (Pd), gold (Au), nickel (Ni), neodymium (Nd), iridium (Ir), chromium (Cr), lithium (Li), calcium (Ca), and an alloy thereof.

In an embodiment, a portion of the light emitted from the emitting layer EML is not transmitted through the first upper electrode CE1, but the light reflected from the first upper electrode CE1 may be again reflected from the reflective layer of the first lower electrode AE1. In such an embodiment, the light emitted from the emitting layer EML may resonate between the reflective layer and the first upper electrode CE1 such that the light extraction efficiency of the display element OLED may be improved by the resonance of the light.

A capping layer ECL may be disposed over the first upper electrode CE1. The capping layer ECL may cover the display element OLED, to and prevent oxygen and moisture from penetrating into the display element OLED. A surface exposed to the outside of the capping layer ECL, i.e., an outer surface of the capping layer ECL may be the display surface DS.

In such an embodiment, the capping layer ECL may be applied to isolate the display element OLED from an external environment, for example, but the disclosure is not limited thereto. In an alternative embodiment, an encapsulating substrate may be applied to isolate the display element OLED from the external environment instead of the capping layer ECL. In such an embodiment, the encapsulating substrate may be combined with the substrate SUB through a sealant. In such an embodiment, where the display element OLED is isolated from the external environment, using the encapsulating substrate, the capping layer ECL may be omitted.

Figure 12A:
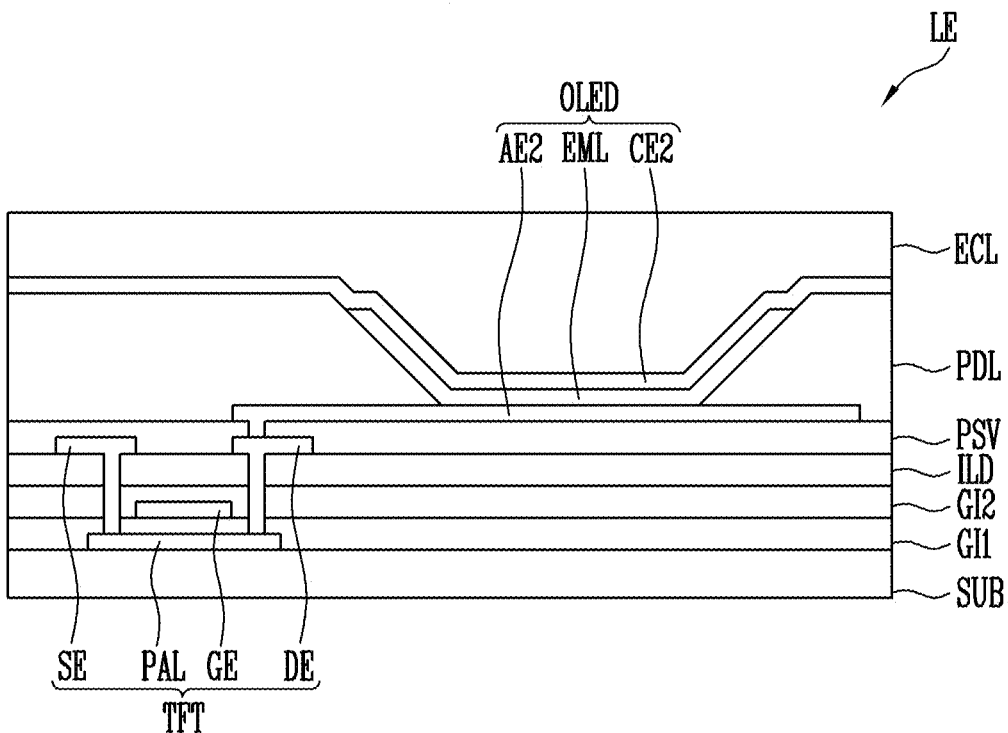
FIGS. 12A and 12B are views illustrating a section of a light emitting part according to embodiments of the disclosure.
Figure 12B:
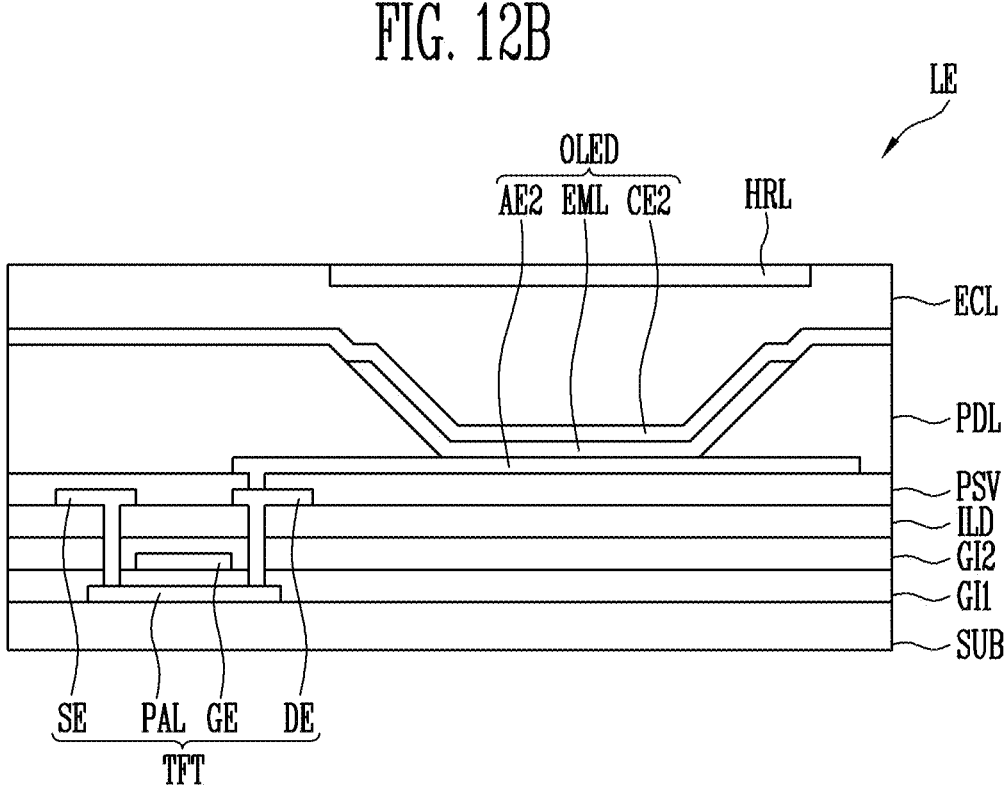

FIGS. 12A and 12B are views illustrating a section of a light emitting part LE according to embodiments of the disclosure. A section of the light emitting part LE and the substrate SUB, which are included in the top part P1, is illustrated in FIGS. 12A and 12B.

Hereinafter, portions different from those of the section of the display pixel PXL shown in FIG. 11 will be mainly described for convenience of description. Therefore, the section of the light emitting part LE shown in FIGS. 12A and 12B may be substantially the same as the embodiment shown in FIG. 11, except those described below.

Referring to FIG. 12A, in an embodiment, a display element OLED may include a second lower electrode AE2 connected to the thin film to transistor TFT, an emitting layer EML disposed on the second lower electrode AE2, and a second upper electrode CE2 disposed on the emitting layer EML. Any one of the second lower electrode AE2 and the second upper electrode CE2 may be an anode electrode, and the other of the second lower electrode AE2 and the second upper electrode CE2 may be a cathode electrode. In one embodiment, for example, the second lower electrode AE2 may be an anode electrode, and the second upper electrode CE2 may be a cathode electrode.

The protective layer PSV may be disposed over the second lower electrode AE2. The second lower electrode AE2 may have a single-layered structure. In one embodiment, for example, the second lower electrode AE2 may include a transparent conductive layer (not shown) capable of allowing light to be transmitted therethrough. The transparent conductive layer may be connected to the drain electrode DE.

The second upper electrode CE2 may be a semi-transmissive reflective layer. In some embodiments, the second upper electrode CE2 may allow light in ultraviolet and visible regions to be transmitted therethrough, and reflect light in an infrared region.

A portion (e.g., infrared light) of the light emitted from the emitting layer EML is not transmitted through the second upper electrode CE2, but the light reflected from the second upper electrode CE2 may be transmitted through the second lower electrode AE2. That is, a portion (e.g., infrared light) of the light emitted from the emitting layer EML may be emitted toward the substrate SUB. Thus, the light emitting part LE may emit light toward the to sensing surface SS.

Referring to FIG. 12B, in an alternative embodiment, a display element OLED may include a second lower electrode AE2 connected to the thin film transistor TFT, an emitting layer EML disposed on the second lower electrode AE2, and a second upper electrode CE2 disposed on the emitting layer EML. Any one of the second lower electrode AE2 and the second upper electrode CE2 may be an anode electrode, and the other of the second lower electrode AE2 and the second upper electrode CE2 may be a cathode electrode. In one embodiment, for example, the second lower electrode AE2 may be an anode electrode, and the second upper electrode CE2 may be a cathode electrode.

The protective layer PSV may be disposed over the second lower electrode AE2. The second lower electrode AE2 may have a single-layered structure. In one embodiment, for example, the second lower electrode AE2 may include a transparent conductive layer (not shown) capable of allowing light to be transmitted therethrough. The transparent conductive layer may be connected to the drain electrode DE.

The second upper electrode CE2 may include a transparent conductive layer (not shown) capable of allowing light to be transmitted therethrough.

A semi-transmissive reflective layer HRL may be disposed on the capping layer ECL. The semi-transmissive reflective layer HRL may be disposed to overlap with the emitting layer EML of the display element OLED.

A portion (e.g., infrared light) of the light emitted from the emitting layer EML is not transmitted through the semi-transmissive reflective layer HRL, but the light reflected from the semi-transmissive reflective layer HRL may be transmitted through the second lower electrode AE2 and the second upper electrode CE2. That is, a portion (e.g., infrared light) of the light emitted from the emitting layer EML may be emitted toward the substrate SUB. Thus, the light emitting part LE may emit light toward the sensing surface SS.

Figure 13:
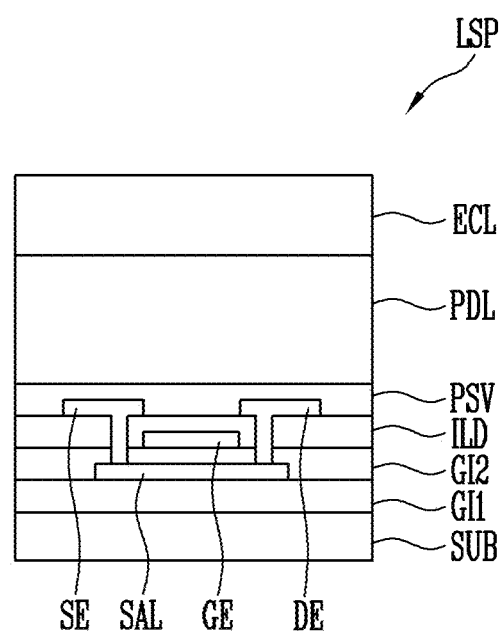
FIG. 13 is a view illustrating a section of a light sensing part according to an embodiment of the disclosure.

FIG. 13 is a view illustrating a section of a light sensing part LSP according to an embodiment of the disclosure.

Hereinafter, portions different from those of the section of the display pixel PXL described in FIG. 11 will be mainly described for convenience of description. Therefore, the section of the light sensing part LSP shown in FIG. 13 may be substantially the same as the embodiment shown in FIG. 11, except those described below.

Referring to FIGS. 1 to 13, in an embodiment, the light sensing part LSP may be disposed on the substrate SUB. The light sensing part LSP may include a sensing semiconductor layer SAL, a gate electrode GE, a source electrode SE, and a drain electrode DE.

The sensing semiconductor layer SAL may be disposed on the first gate insulating layer GI1.

The sensing semiconductor layer SAL may generate a sensing current, corresponding to light (e.g., infrared light) incident from the outside. In one embodiment, for example, the sensing semiconductor layer SAL may to generate a sensing current, corresponding to light (e.g., infrared light) incident through the sensing surface SS.

In one embodiment, for example, the sensing semiconductor layer SAL may include amorphous Si—Ge. In the sensing semiconductor layer SAL, regions connected to the source electrode SE and the drain electrode DE may be source and drain regions doped or injected with an impurity. In the sensing semiconductor layer SAL, a region between the source region and the drain region may be a channel region.

Although not shown in FIG. 13, an ohmic contact layer (not shown) may be disposed on the sensing semiconductor layer SAL.

The second gate insulating layer GI2 may be v over the sensing semiconductor layer SAL. The second gate insulating layer GI2 may cover the sensing semiconductor layer SAL, and isolate the sensing semiconductor layer SAL and the gate electrode GE from each other.

The gate electrode GE may be disposed on the second gate insulating layer GI2. The gate electrode GE may overlap with the sensing semiconductor layer SAL. The gate electrode GE may block external light incident into the sensing semiconductor layer SAL from the display surface DS.

The interlayer insulating layer ILD may be disposed over the gate electrode GE. The interlayer insulating layer ILD may insulate the gate electrode GE from the source electrode SE and the drain electrode DE.

In such an embodiment, the source and drain regions of the sensing semiconductor layer SAL may be exposed via contact holes defined to through the second gate insulating layer GI2 and the interlayer insulating layer ILD.

The source electrode SE and the drain electrode DE may be disposed on the interlayer insulating layer ILD to be spaced apart from each other.

The other end of the source electrode SE may be connected to the source region through one of the contact holes.

One end of the drain electrode DE may be connected to the drain region through another of the contact holes.

The protective layer PSV, the pixel defining layer PDL, and the capping layer ECL may be disposed over the source electrode SE and the drain electrode DE.

The display pixel PXL, the light emitting part LE, and the light sensing part LSP, which are respectively shown in FIGS. 11 to 13, may be implemented on the substrate SUB included in the top part P1. In such an embodiment, the light sensing part LSP shown in FIG. 13 may be implemented on the substrate SUB included in the bottom part P2.

According to embodiments of the disclosure, the electronic device may effectively sense a movement of a finger, based on a nail image.

Further, according to embodiments of the disclosure, the electronic device may substantially improve user convenience.

Further, according to embodiments of the disclosure, the electronic device may effectively sense a heartbeat of a user.

The invention should not be construed as being limited to the embodiments set forth herein. Rather, these embodiments are provided so that this disclosure will be thorough and complete and will fully convey the concept of the invention to those skilled in the art.

While the invention has been particularly shown and described with reference to exemplary embodiments thereof, it will be understood by those of ordinary skill in the art that various changes in form and details may be made therein without departing from the spirit or scope of the invention as defined by the following claims.

What is claimed is:

1. An electronic device adapted to be mounted around a finger, the electronic device comprising:
   a top part adapted to cover a nail of the finger and having a display area and a sensing area;
   a bottom part disposed opposite to the top part, wherein the bottom part is configured to contact a fingerprint surface of the finger; and
   a side part connecting the top part and the bottom part to each other,
   wherein the top part comprises a first substrate, display pixels, light emitting parts, and light sensing parts, and wherein the display pixels, the light emitting parts, and the light sensing parts are disposed on the first substrate,
   wherein each of the display pixels includes a pixel semiconductor layer disposed on the first substrate, a first gate electrode overlapping with the pixel semiconductor layer, and a first gate insulating layer disposed between the pixel semiconductor layer and the first gate electrode,
   wherein each of the light sensing parts includes a sensing semiconductor layer disposed on the first gate insulating layer, a second gate electrode overlapping with the sensing semiconductor layer, and a second gate insulating layer disposed between the sensing semiconductor layer and the second gate electrode,
   wherein the top part is configured to generate a nail image by image-picking up the nail using the light emitting parts and the light sensing parts, in conjunction with using a controller and an image analyzer, and is configured to sense a state of the finger pressing on the bottom part, based on the nail image, and wherein information from the image analyzer reflecting the state of the finger pressing on the bottom is displayed in the display area.

2. The electronic device of claim 1,
   wherein the first substrate includes the display area and the sensing area;
   wherein the display pixels are disposed in the display area, and the display pixels display an image through a display surface which is a front surface of the top part,
   wherein the light emitting parts are disposed in the sensing area, and emit light onto the nail through a sensing surface which is a back surface of the top part,
   wherein the light sensing parts are disposed in the sensing area, and sense reflected light through the sensing surface, and
   wherein the reflected light is the light emitted from the light emitting parts and reflected by the nail.

3. The electronic device of claim 2, wherein the display area and the sensing area do not overlap with each other.

4. The electronic device of claim 2, wherein the display area and the sensing area overlap with each other.

5. The electronic device of claim 2, wherein the second gate electrode blocks external light which is transmitted through the display surface, to the sensing semiconductor layer.

6. The electronic device of claim 2, wherein
   the pixel semiconductor layer includes polycrystalline Si, and
   the sensing semiconductor layer includes amorphous Si—Ge.

7. The electronic device of claim 2, wherein
   a display element included in each of the display pixels includes:
   a first lower electrode including a transparent conductive layer and a reflective layer;
   a first emitting layer disposed on the first lower electrode; and
   a first upper electrode disposed on the first emitting layer, and
   a display element included in each of the light emitting parts includes:
   a second lower electrode including the transparent conductive layer;
   a second emitting layer disposed on the second lower electrode; and
   a second upper electrode disposed on the second emitting layer.

8. The electronic device of claim 7, wherein each of the first upper electrode and the second upper electrode is a semi-transmissive reflective layer which reflects light in an infrared region.

9. The electronic device of claim 7, wherein
   the display element included in each of the light emitting parts further includes a semi-transmissive reflective layer disposed on the second upper electrode,
   wherein the semi-transmissive reflective layer overlaps with the second emitting layer, and
   wherein the semi-transmissive reflective layer reflects light in an infrared region.

10. The electronic device of claim 9, wherein the display element included in each of the light emitting parts further includes a capping layer disposed between the second upper electrode and the semi-transmissive reflective layer.

11. The electronic device of claim 2, wherein the bottom part, in conjunction with the controller and the image analyzer, is adapted to generate a biometric image by image-picking up the fingerprint surface, and adapted to sense a heartbeat of a user, based on the biometric image.

12. The electronic device of claim 11, wherein the bottom part includes:
   a second substrate including an auxiliary area; and
   additional light sensing parts disposed in the auxiliary area, wherein the additional light sensing parts sense transmitted light through an auxiliary surface which is a front surface of the bottom part,
   wherein the transmitted light is the light emitted from the light emitting parts and transmitted through the finger.

13. The electronic device of claim 2, wherein the light emitted from the light emitting parts is infrared light.

* * * * *